United States Patent [19]

Dawe

[11] 4,432,762
[45] Feb. 21, 1984

[54] VOLUMETRIC DROP DETECTOR

[75] Inventor: Garfield A. Dawe, Lindenhurst, Ill.

[73] Assignee: Abbott Laboratories, North Chicago, Ill.

[21] Appl. No.: 423,370

[22] Filed: Sep. 24, 1982

Related U.S. Application Data

[63] Continuation of Ser. No. 276,120, Jun. 22, 1981, abandoned.

[51] Int. Cl.³ .............................................. A61M 5/16
[52] U.S. Cl. .................................. 604/253; 73/861.41; 250/560
[58] Field of Search ................... 604/253, 251, 65, 50; 73/861.41, 861, 55; 250/560, 561; 222/420, 422

[56] References Cited

U.S. PATENT DOCUMENTS

| | | | |
|---|---|---|---|
| 2,880,764 | 4/1959 | Pelavin | 141/130 |
| 3,500,366 | 3/1970 | Chesney et al. | 340/222 |
| 3,563,090 | 2/1971 | Deltour | 73/194 |
| 3,815,414 | 6/1974 | Hellstrom | 73/861.41 |
| 3,826,137 | 7/1979 | Clarke | 73/194 |
| 3,898,637 | 8/1975 | Wolstenholme | 34/239 |
| 4,038,982 | 8/1977 | Burke et al. | 128/DIG. 13 |
| 4,088,411 | 5/1978 | Ahlquist et al. | 250/560 X |
| 4,152,767 | 5/1979 | Laliotis | 250/560 X |
| 4,314,484 | 2/1982 | Bowman | 73/861.41 |

Primary Examiner—Stephen C. Pellegrino
Attorney, Agent, or Firm—Neil E. Hamilton

[57] ABSTRACT

A device for measuring the volume of flow in a liquid conveying apparatus wherein drops of the liquid are formed and directed into a length of measurement tubing having a known internal diameter. As the drop is passed through the measurement tubing its length is determined by a combined optoelectronic mechanism including drop length sensors. The drop forming portion and measurement tubing can be manufactured from inexpensive resinous materials making these portions disposable and particularly adaptable to intravenous administration.

17 Claims, 4 Drawing Figures

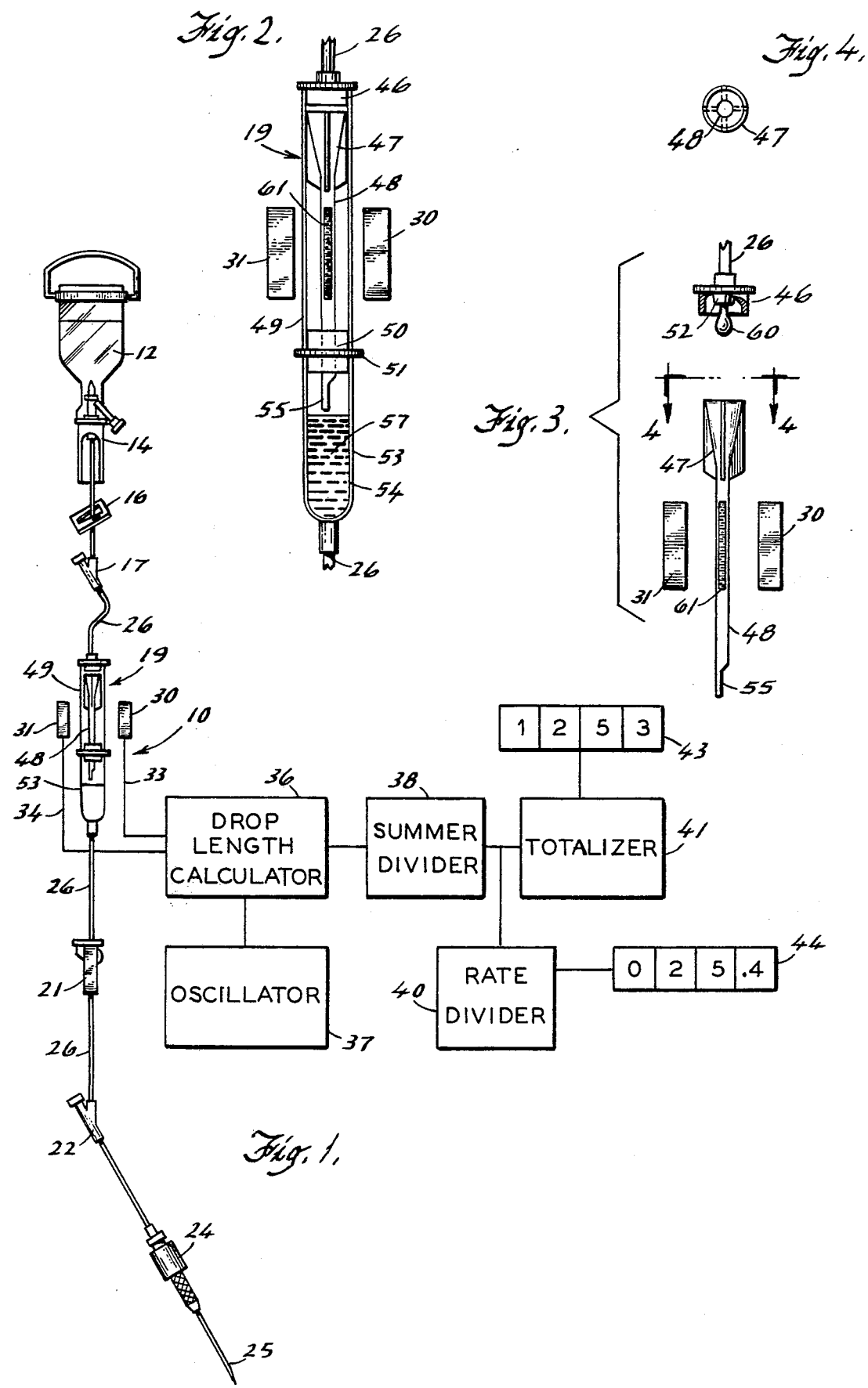

VOLUMETRIC DROP DETECTOR

This is a continuation of application Ser. No. 276,120, filed June 22, 1981, now abandoned.

BACKGROUND OF THE INVENTION

This invention relates to an apparatus for monitoring the rate of liquid flow in a liquid conveying apparatus. More particularly, this invention relates to an apparatus for measuring the drop volume of a liquid in an I.V. administration set by utilizing a section of relatively narrow tubing into which the drops are directed and the length of the drop is optically and electronically measured.

A flow rate measuring device of the general type concerned with in this invention is described in U.S. Pat. No. 3,826,167. In this particular patent, an apparatus is described for measuring liquid flow which employs a capillary tube into which a liquid flows from a nozzle forming a stream of drops. The drops then freely fall from a nozzle where they are counted prior to falling into the capillary tube. By placing the nozzle in such a manner that the drops contact the surface of the liquid in the tubing, a drop forming gap is provided which is stated to afford accurate determination of the drop count. As there is no detection means associated with the particular drop forming mechanism, this must be done manually. In U.S. Pat. No. 3,898,637, a detection means for gas entering a human blood system from extra-corporeal tubing is described. In this particular unit, electronic detection means is afforded and placed in conjunction with a controlled restriction for the purpose of air bubble detection.

The prior art does not provide an accurate method of measuring the volume of liquid in an I.V. administration set. The prior art is either concerned with methods of forming drops of liquid, which must be manually counted, or with an electronic detection means used to restrict bubbles in a bubble detection system.

It is an advantage of the present invention to provide a means of monitoring I.V. medication by drop rate methods in a manner which actually measures the drop volume of the flow of liquid. Other advantages are a volumetric drop measuring flow meter which is easily adapted to I.V. administration apparatus; can be utilized in conjunction with the usual I.V. administration drip chamber; can be manufactured in such a manner that the disposable portion is relatively inexpensive; and lends itself to be easily integrated with various electronic functions.

SUMMARY OF THE INVENTION

The foregoing advantages are accomplished and the shortcomings of the prior art are overcome by the improved volumetric drop detector disclosed, wherein a liquid drop forming means is utilized in conjunction with a length of measurement tubing having a known internal diameter. Optoelectronic means are positioned with respect to the measurement tubing to determine the length of the drop. Collecting means are disposed with respect to the measurement tubing to receive the measured drops. Tube connector means are provided in conjunction with the drop forming means and the collecting means for connection with first and second lengths of flexible tubing normally associated with an I.V. administration set. In order to direct the liquid drops from the drop forming means into the measurement tubing, a funnel member is provided, forming an upper extending portion of the measurement tubing. The preferred optical-electronic means associated with respect to the measurement tubing are two drop length sensors which are operatively connected to a drop length calculator as well as an oscillator. A summer divider is electrically connected to the drop length calculator and in turn to a totalizer which can render a digital reading of the volume delivered. If desired, a rate divider can be interconnected to the summer divider to give a digital reading of the delivery rate.

BRIEF DESCRIPTION OF THE DRAWINGS

A better understanding of the volumetric drop detector of this invention will be accomplished by reference to the drawings wherein:

FIG. 1 is a view in side elevation of the volumetric drop detecting mechanism shown in conjunction with a standard I.V. administration set and indicating the optical and electronic components in schematic form.

FIG. 2 is an enlarged view of the measurement tubing for the drops and showing it combined with an I.V. drip chamber.

FIG. 3 is a view in side elevation showing the drop measurement tubing with a funnel portion in conjunction with the drop forming member and illustrating the form of the drop as it passes through the measurement tubing.

FIG. 4 is a view in horizontal section taken along line 4—4 of FIG. 3.

DESCRIPTION OF THE PREFERRED EMBODIMENT

Proceeding to a detailed description of the preferred embodiment of the present invention, the volumetric drop detector 10 is shown for use in conjunction with a standard parenteral administration unit composed of a solution container 12, the contents of which are connected by and made accessible through a vented piercing pin 14. The usual length of tubing 26 extends from vented piercing pin 14 to a drop forming and measurement means 19. The usual Y-reseal injection site is afforded at 17 and the flow of fluid to the drop forming measurement means can be terminated by slide clamp 16. Extending from the opposing end of drop forming and measurement means 19 is a similar length of flexible tubing 26 to which is attached a standard roller flow control clamp 21 with another Y-injection site 22 disposed between needle adapter 24 with hypodermic needle 25 and the clamp 21.

The volumetric drop detector 10 includes liquid drop forming and measurement means 19 as well as oppositely positioned, optical drop length sensors 30 and 31. These optical sensors are interconnected to a drop length calculator 36 the signals of which are expressed in digital format developed by the oscillator 37. A summer divider 38 receives signals from the drop length calculator 36 which in turn is connected to a totalizer 41. A digital display unit 43 is provided to give a digital readout from the totalizer. Also interconnected to the summer divider is a rate divider 40 which also has a digital delivery rate display 44 operatively connected to it.

Referring to FIG. 2, it will be seen that the drop forming and measurement means 19 includes measurement tubing 48 having a funnel portion 47 at one end and a discharge tip 55 at the other. A drop forming or drip means 46 also serves as a connecting means for tubing 26 at the upper end as well as an annular, fluid-tight attachment for tubing housing 49. A centering sleeve 50 for tubing 48 also serves as an attachment for chamber 53 to which is secured a second length of tubing 26. Chamber 53 serves as a collecting means for I.V. solution 57 whereas funnel portion 47 in conjunction with drop forming means 46 will serve as a drip chamber 54.

FIG. 3 illustrates the formation of a drop of liquid 60 from drop forming means 46 which will be effected through the drop forming nozzle 52 axially aligned with respect to funnel portion 47 of measurement tubing 48. The numeral 61 shows an elongated liquid drop as it would be formed due to the internal diameter of measurement tubing 48. Preferably, this section of tubing is formed from a nonwetting plastic material and preferably polypropylene so as to present a nonwetting surface for the liquid. The preferred internal diameter is approximately 2.28 mm and the preferred length is 6 cm.

OPERATION

A better understanding of the advantages of the volumetric drop detector of this invention will be had by a description of its operation. It should be pointed out that a key factor in the operation of the drop detector is in knowing the internal diameter of measurement tubing 48. Once this is established, a standard unit of volume can be obtained by measuring the length of the drop. The drop forming and measuring means 19 which will have the measurement tubing 48 contained therein, will be supplied to a component in the usual I.V. administration set. This will include a vented piercing pin 14, a slide clamp 16, as well as a Y reseal injection site 17. When it is desired to administer the contents of solution container 12, the vented piercing pin will be placed in fluid communication with the contents of container 12 and liquid will flow through tubing 26 and to drop forming means 46. A drop forming and measurement means 19 will have been placed and secured between oppositely positioned drop length sensors 30 and 31 so that they are aligned in a parallel manner with measurement tubing 48. The drop length sensors may be capacitance plates, optical arrays, time-of-flight, shadow graph, etc. so long as it gates the oscillator frequency to produce a train of pulses equal to the drop length. In this instance, the preferred drop length sensors are of the time-of-light type and are at least as long as the longest liquid column to be measured. They preferably are 2 cm in length. Selection of a normal drop length can be made such that the controlled inside diameter of the drop measuring tube 48 will give a standard unit of volume. For example, a drop length of 1.62 cm. in a tube with a 0.114 cm radius will equal a volume of 0.067 cc or 1/15th cc. If the oscillator frequency is designed to produce 100 pulses for a "normal" drop length of 1.62 cm., and as the length is directly related to volume, each pulse represents 1% of 0.067 cc. A small drop may produce 80 pulses and a large drop 120 pulses but summing the pulses as provided by summer divider 38 and divided by the rate divider 40 which will divide by 100 will yield output signals each equal to exactly 0.067 cc. Finally, the signals representing, for example, 0.067 cc. increments, are divided by 15 and displayed on counter 43 as the total volume in cc. They are also sampled for a period of time to give the rate of delivery as indicated at 44.

It will be appreciated that the monitoring or controlling of I.V. medication by drop rate methods has always been limited by the variability of drop size. Viscosity, surface tension, rate of growth and other factors spread the range of drop volumes well over plus or minus 30%. The volumetric drop detector, as disclosed herein, measures the drop volume by a unique method of capturing the fluid of a given drop inside a section of tubing which has a known cross-section and then determining its length through the use of drop length sensors and other functional circuit modules.

It will be appreciated that while in the foregoing description certain functional circuit modules are indicated in block diagrams, microprocessor technology could readily be adapted for purposes of calculating the length of the drops as well as indicating delivery rate and volume delivered. Further, while the volumetric drop detector has been disclosed for use in an I.V. administration set, it will be appreciated that the flow meter is readily adaptable outside the medical field and could be utilized to accurately monitor or control liquid flow where an inexpensive disposable element can be advantageously utilized such as in any liquid conveying apparatus.

In the foregoing description, the measuring tubing 48 was described as being composed of a polypropylene resin material. If desired, other materials which would provide a nonwetting surface and can be formed with a small bore diameter, could be substituted, such as Teflon or glass. Further, while the diameter of tubing 48 was indicated as being 2.28 mm. in inside diameter, this diameter could range from 1 mm. to 5 mm. While the preferred length of tubing 48 is 60 mm. this could vary from 5 mm. to 130 mm. Similarly, other industrial applications especially those of highly viscous materials may utilize larger drop volumes and consequently larger diameter conduit.

It will thus be recognized that there is now provided a volumetric measuring flow meter which can accurately determine the volume of a liquid by utilizing standard electronic components in conjunction with a length of tubing having a known internal diameter. The unit can be provided so that the measuring tubing and its housing are disposable, which will lend itself to use in a disposable I.V. administration apparatus. The volumetric drop detector can be used outside the medical field, such as in any apparatus where precise volumetric flow detection is desired.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. A volumetric drop detector for use with a liquid conveying apparatus including the usual first and second flow paths comprising:
   liquid drop forming means;
   a length of measurement tubing having a known internal diameter;
   means operatively associated with said drop forming means to direct liquid drops into measurement tubing;
   optoelectronic means operatively positioned with respect to said measurement tubing to determine the length of said drop;
   collecting means positioned from said measurement tubing to receive said measured drops; and connector means operatively associated with said drop forming means and said collecting means for connection with said first and second flow paths.

2. The volumetric drop detector as defined in claim 1 wherein said means to direct liquid drops into said measurement tubing is defined by a funnel portion connected to said measurement tubing.

3. The volumetric drop detector as defined in claim 2 wherein said collecting means is defined by a chamber and said measurement tubing provides a drop discharging means at the end thereof.

4. The volumetric drop detector as defined in claim 3 further including a tubular housing member positioned to surround said measurement tubing and said funnel member, said tubular housing in fluid tight engagement with said collecting means at one end and said connector means for said drop forming means at the other, said drop forming means and said tubular housing defining a drip chamber.

5. The volumetric drop detector as defined in claim 4 wherein said collecting means is defined by a chamber member and further including a centering sleeve operatively contacting said measurement tubing and said tubular housing as well as said chamber member.

6. The volumetric drop detector as defined in claim 4 further including a liquid container connection means secured to said first flow path opposite said drip chamber and an intravenous delivery device secured to said second flow path opposite said chamber member.

7. A volumetric drop detector for use with an intravenous administration apparatus including the usual first and second lengths of flexible tubing comprising:
  liquid drop forming means;
  a length of measurement tubing having a known internal diameter;
  means operatively associated with said drop forming means to direct liquid drops into said measurement tubing;
  optoelectronic means including two operatively positioned drop length sensors operatively positioned with respect to said measurement tubing to determine the length of said drop;
  collecting means positioned from said measurement tubing to receive said measured drops; and
  tubing connector means operatively associated with said drop forming means and said collecting means for connection with said first and second lengths of flexible tubing.

8. The volumetric drop detector as defined in claim 7 wherein said optoelectronic means further includes:
  a drop length calculator;
  an oscillator;
  a summer divider; and
  a totalizer;
  said drop length calculator, oscillator, summer divider and totalizer all operatively connected to provide a digital readout of the volume delivered.

9. The volumetric drop detector as defined in claim 8 further including a rate divider operatively connected to said summer divider to provide a digital readout of the delivery rate.

10. The volumetric drop detector as defined in claim 7 wherein said measurement tubing is composed of a polypropylene resin material.

11. The volumetric drop detector as defined in claim 10 wherein said measurement tubing has an internal diameter in the range of about 1 mm to about 130 mm.

12. A disposable device for monitoring or controlling liquid flow having first and second flow paths, said device for use with an optoelectronic device to determine the length of a drop of liquid flowing therein comprising:
  liquid drop forming means;
  a length of measurement tubing have a known internal diameter;
  means operatively associated with said drop forming means to direct liquid drops into said measurement tubing;
  collecting means positioned from said measurement tubing to receive said measured drops; and
  connector means operatively associated with said drop forming means and said collecting means for connection with said first and second flow paths.

13. The disposable device as defined in claim 12 wherein said means to direct liquid drops into said measurement tubing is defined by a funnel portion connected to said measurement tubing.

14. The disposable device as defined in claim 13 wherein said disposable device forms a part of a disposable I.V. administration set and said collecting means is defined by a chamber and said measurement tubing provides a drop discharging means at the end thereof.

15. The disposable I.V. administration set as defined in claim 14 further including a tubular housing member positioned to surround said measurement tubing and said funnel member, said tubular housing in fluid tight engagement with said collecting means at one end and said connector means for said drop forming means at the other, said drop forming means and said tubular housing defining a drip chamber.

16. The disposable I.V. administration set as defined in claim 15 wherein said collecting means is defined by a chamber member and further including a centering sleeve operatively contacting said measurement tubing and said tubular housing as well as said chamber member.

17. The disposable I.V. administration set as defined in claim 15 further including a liquid container connection means secured to said first flow path opposite said drip chamber and an intravenous delivery device secured to said second flow path opposite said collecting means.

* * * * *